United States Patent [19]

Broecker et al.

[11] 4,298,766

[45] Nov. 3, 1981

[54] PREPARATION OF 2-METHYL-PENTANE-2,4-DIOL

[75] Inventors: Franz J. Broecker; Karl G. Baur, both of Ludwigshafen; Rolf Platz, Mannheim; Joachim Stabenow, Weinheim, all of Fed. Rep. of Germany

[73] Assignee: BASF Aktiengesellschaft, Fed. Rep. of Germany

[21] Appl. No.: 76,392

[22] Filed: Sep. 17, 1979

[30] Foreign Application Priority Data

Oct. 2, 1978 [DE] Fed. Rep. of Germany ....... 2842942

[51] Int. Cl.³ ............................................. C07C 29/136
[52] U.S. Cl. .................................. 568/862; 252/466 J
[58] Field of Search ................ 568/846, 862; 252/443, 252/466 J

[56] References Cited

U.S. PATENT DOCUMENTS 3,932,534  1/1976  Fukunaga et al. ................ 252/466 J

FOREIGN PATENT DOCUMENTS 1182797  3/1970  United Kingdom .

*Primary Examiner*—Natalie Trousof
*Assistant Examiner*—L. Hendriksen
*Attorney, Agent, or Firm*—Keil & Witherspoon

[57] ABSTRACT

A process for the preparation of 2-methyl-pentane-2,4-diol by hydrogenating diacetone-alcohol at an elevated temperature in the presence of a catalyst which has been obtained by calcining the compound of the formula $Ni_6Al_2(OH)_{16}CO_3 \cdot 4H_2O$.

1 Claim, 1 Drawing Figure

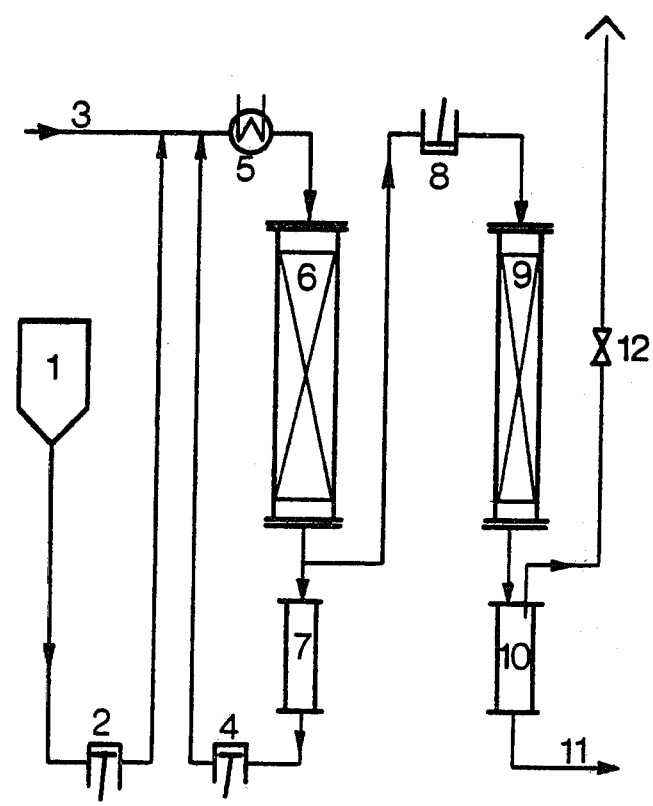

PREPARATION OF 2-METHYL-PENTANE-2,4-DIOL

The present invention relates to a novel process for the preparation of 2-methyl-pentane-2,4-diol by catalytically hydrogenating diacetone-alcohol. 2-Methyl-pentane-2,4-diol is in the main used as a fuel additive.

Diacetone-alcohol which, as is known, may be prepared by alkaline condensation of acetone, can be converted into 2-methyl-pentane-2,4-diol by hydrogenation.

Since diacetone-alcohol is chemically and thermally very unstable, the hydrogenation requires special measures in order to minimize the formation of by-products.

According to the process described in British Pat. No. 1,182,797, diacetone-alcohol is hydrogenated in the presence of Raney nickel under atmospheric pressure at from 50° to 100° C. The Examples show that the selectivity of the hydrogenation is unsatisfactory. Thus, even at relatively low temperatures of from 50° to 80° C., 19.9% of isopropanol and acetone are formed, with only from 62.5% to a maximum of 83% of the desired 2-methyl-pentane-2,4-diol. This shows how difficult it is to achieve a high selectivity in converting the relatively unstable diacetone-alcohol into the diol.

We have found that 2-methyl-pentane-2,4-diol can be prepared particularly advantageously by catalytic hydrogenation of diacetone-alcohol at an elevated temperature if a catalyst is used which has been obtained by calcining the compound of the formula $Ni_6Al_2(OH)_{16}CO_3.4H_2O$.

The catalyst used according to the invention is prepared by calcining the compound of the formula $Ni_6Al_2(OH)_{16}CO_3.4H_2O$, which serves as the catalyst intermediate. This intermediate may be prepared, for example, by stoichiometric reaction of aqueous solutions of nickel salts and aluminum salts, advantageously the nitrates, precipitation at an alkaline pH, for example by adding an alkali metal carbonate, isolation and drying. The compound of the above formula is then calcined, whereby it is converted to an oxide mixture. Calcination is effected, for example, by heating for from 5 to 24 hours at from 300° to 450° C., preferably from 350° to 400° C.

It is advantageous to mold the catalyst, for example into tablets, and to reduce it with hydrogen prior to the hydrogenation according to the invention. In the conventional preparation of pills, it is advantageous to add up to 2% by weight of graphite, as a lubricant, to the finely divided catalyst. The pre-reduction is carried out, for example, by treating the catalyst with hydrogen, for example for from 12 to 60 hours at from 300° to 450° C., advantageously from 350° to 400° C., preferably after the catalyst has been introduced into the hydrogenation reactor which is to be used.

The catalyst used according to the invention exhibits, even at relatively low temperatures and pressures, a substantially higher activity and selectivity than other supported nickel catalysts.

The hydrogenation according to the invention is carried out at from 50° to 120° C., preferably from 60° to 100° C., under a pressure of from 1 to 300 bar, preferably from 30 to 200 bar, advantageously in a trickle reactor.

In a particularly advantageous embodiment of the invention, the hydrogenation is carried out, as illustrated in the FIGURE, by the trickle method, using two reactors equipped with catalyst.

The starting material to be hydrogenated is fed from the vessel (1), by means of a metering pump (2), into the hydrogenation circulation, together with hydrogen (3). The hydrogenation circulation is maintained by means of a circulation pump (4). The desired reactor input temperature is obtained by means of a heat exchanger (5). The liquid then trickles, under a particular partial pressure of $H_2$, over the catalyst bed of the first reactor (6), and in doing so undergoes hydrogenation. A part of the hydrogenation solution is discharged from the circulation system via the downstream constant-level device (7) and passes, via a heat exchanger (8), into the second hydrogenation reactor (9), which is operated without recycling. The product is discharged (11) via a constant-level device and at the same time off-gas is released via a valve (12) at the separator (10). The first reactor (6) is operated with a high recycling ratio, ie. there is a large circulation of liquid, the throughput per unit cross-sectional area of catalyst being from 20 to 60 $[m^3/m^2].h$.

As a result, even in the first reactor (6) the temperature differential is low, even though the conversion is >89%. The downstream second reactor (9) is operated as a single passage, without recycling, and gives a completely hydrogenated product.

The recycle ratio $$\frac{\text{Weight of amount recycled}}{\text{Weight of amount recycled + weight of feed}}$$

in the first reactor is advantageously from 0.900 to 0.995, preferably from 0.930 to 0.990.

In the novel process, because of the high catalyst activity, 2-methyl-pentane-2,4-diol can be obtained in high yield and with high selectivity at relatively low temperatures and pressures.

EXAMPLES 1 TO 3

Preparation of the Catalyst 279.4 kg of $Ni(NO_3)_2.6H_2O$ and 120 kg of $Al(NO_3)_3.9H_2O$ are dissolved in water to give a volume of solution of 640 liters. A second solution is then prepared by dissolving 159 kg of technical-grade sodium bicarbonate in sufficient water to give a volume of 750 liters. Sufficient water to ensure that the mixture obtained subsequently is easily stirrable is introduced into a precipitation vessel.

The two solutions, and the initial charge of water, are separately heated to 80° C. The initial charge of water is then brought to pH 8.0 by adding a little of the second solution, whilst stirring. The precipitation is carried out at 80° C. and a pH of 8.0 by simultaneously running both solutions into the initial charge. After completion of precipitation, stirring is continued for 15 minutes at 80° C. and the precipitate is then filtered off. The product thus obtained is washed with water until nitrate is no longer detectable in the filtrate. The washed residue is dried at 110° C. It has the formula $Ni_6Al_2(OH)_{16}CO_3.4H_2O$. This catalyst intermediate is then calcined by heating for from 5 to 24 hours at 350° C. When the catalyst has cooled, it is mixed with 2 percent by weight of graphite and the mixture is compression-molded to form pills of size 3×3 mm.

Preparation of 2-methyl-pentane-2,4-diol

The hydrogenation is carried out in a trickle reactor with recycling. 200 ml of the catalyst are introduced into the trickle reactor. The catalyst is treated with hydrogen for 24 hours at 400° C. It is then cooled to the reaction temperature shown in the Table and a mixture of the composition shown below is pumped in, whilst at the same time introducing hydrogen.

| | | |
|---|---|---|
| Diacetone-alcohol | : 97.92 | [% by weight] |
| 2-Methyl-pentane-2,4-diol | : 0.17 | " |
| Mesityl oxide | : 0.38 | " |
| Isopropanol | : 0.84 | " |
| Acetone | : 0.66 | " |

The hydrogenation product is discharged continuously at the reactor outlet via the constant-level device.

The reaction conditions and results are shown in the Table.

COMPARATIVE EXAMPLES a TO c (a) The procedure followed is similar to the Examples described above, except that the catalyst used comprises 200 ml of a nickel silicate catalyst, containing 70% by weight of NiO and 30% by weight of $SiO_2$, in the form of 3×3 mm pills. The reaction conditions and results are shown in the Table. It will be seen that even at a higher temperature than in Example 2 the conversion is only 73.9%. The selectivity of only 87.5% is attributable to increased formation of mesityl oxide (7.4%).

(b) and (c) The procedure followed is in accordance with the data in the Examples described above, except that the catalyst used comprises 200 ml of a cobalt-/aluminum oxide catalyst containing 75% by weight of cobalt oxide and 25% by weight of aluminum oxide, in the form of 3×3 mm pills, and is reduced, before the reaction, for 24 hours at 400° C. with a mixture of 95% by volume of nitrogen and 5% by volume of hydrogen. The reaction conditions and results are shown in the Table.

As may be seen, the yields of 2-methyl-pentane-2,4-diol are poor. The selectivity at 60° C. is only 45.5% and decreases with increasing temperature. The poor results are attributable to the extensive decomposition of diacetone-alcohol to acetone. Part of the acetone then undergoes hydrogenation to isopropanol.

TABLE

| Example No. | Temperature [°C.] | Pressure [bar] | Throughput [liter/liter of catalyst.h]h] | Recycle ratio | Analysis of the hydrogenation product [% by weight] | | | | | Yield of 2-methyl-pentane-2,4-diol [%] | Conversion [%] | Selectivity |
|---|---|---|---|---|---|---|---|---|---|---|---|---|
| | | | | | Diacetone-alcohol | 2-Methyl-pentane-2,4-diol | Acetone | Isopropanol | Mesityl oxide | | | |
| 1 | 70 | 30 | 0.5 | 0.990 | 10.4 | 86.0 | 0.3 | 1.9 | 0.8 | 86.4 | 89.3 | 96.8 |
| 2 | 90 | 100 | 1.0 | 0.980 | 10.5 | 86.9 | — | 1.4 | 1.1 | 87.2 | 89.3 | 97.6 |
| 3 | 90 | 200 | 0.5 | 0.990 | 3.3 | 93.4 | 0.1 | 1.1 | 2.0 | 93.7 | 96.7 | 96.8 |
| a | 100 | 100 | 1.0 | 0.980 | 25.8 | 65.1 | — | 1.0 | 7.4 | 64.7 | 73.9 | 87.5 |
| b | 60 | 30 | 0.5 | 0.990 | 25.4 | 34.0 | 16.3 | 22.0 | 0.4 | 33.8 | 74.3 | 45.5 |
| c | 80 | 30 | 1.5 | 0.971 | 37.4 | 20.3 | 22.6 | 16.7 | 0.3 | 20.2 | 62.2 | 32.5 |

We claim:

1. A process for the preparation of 2-methyl-pentane-2,4-diol by catalytically hydrogenating diacetone-alcohol at an elevated temperature, wherein a catalyst obtained by heating a compound of the formula $Ni_6Al_2(OH)_{16}CO_3 \cdot 4H_2O$ for from 5 to 24 hours at from 300° to 450° C. and treating the resulting product with hydrogen for from 12 to 60 hours at from 300° to 450° C. is used and wherein the hydrogenation is carried out at a pressure of from 1 to 300 bar and at from 50° to 120° C. in two trickle reactors, the first reactor being operated with recycling and the second reactor without recycling.

* * * * *